United States Patent
Robins et al.

(10) Patent No.: US 9,551,018 B2
(45) Date of Patent: Jan. 24, 2017

(54) PROCESS FOR THE PREPARATION OF OPTICALLY ACTIVE CHIRAL AMINES

(71) Applicant: LONZA AG, Visp (CH)

(72) Inventors: Karen Robins, Visp (CH); Uwe Scheuer, Greifswald (DE); Matthias Höhne, Bandelin (DE)

(73) Assignee: LONZA AG, Visp (CH)

( * ) Notice: Subject to any disclaimer, the term of this patent is extended or adjusted under 35 U.S.C. 154(b) by 0 days.

(21) Appl. No.: 14/740,646

(22) Filed: Jun. 16, 2015

(65) Prior Publication Data

US 2015/0284752 A1     Oct. 8, 2015

Related U.S. Application Data

(62) Division of application No. 12/223,730, filed as application No. PCT/EP2007/001222 on Feb. 13, 2007, now Pat. No. 9,074,228.

(30) Foreign Application Priority Data

Feb. 13, 2006    (EP) ..................................... 06002859

(51) Int. Cl.
| | | |
|---|---|---|
| C12P 13/00 | (2006.01) | |
| C12N 9/10 | (2006.01) | |
| C12P 17/10 | (2006.01) | |
| C12P 13/02 | (2006.01) | |
| C12P 13/06 | (2006.01) | |
| C12P 13/22 | (2006.01) | |

(52) U.S. Cl.
CPC .............. *C12P 17/10* (2013.01); *C12N 9/1096* (2013.01); *C12P 13/001* (2013.01); *C12P 13/02* (2013.01); *C12P 13/06* (2013.01); *C12P 13/22* (2013.01); *C12Y 206/01018* (2013.01)

(58) Field of Classification Search
CPC ............................ C12N 9/1096; C12P 13/001
See application file for complete search history.

(56) References Cited

U.S. PATENT DOCUMENTS 6,936,444 B1 * 8/2005 Bartsch ......................... 435/106
8,728,750 B2 * 5/2014 Robins et al. .................. 435/16

FOREIGN PATENT DOCUMENTS

EP     1889907 B1     9/2009

OTHER PUBLICATIONS

Shin et al. Biotechnology and Bioengineering, vol. 65, 1999, pp. 206-211.*
Juni et al. J. Biol. Chem. 1956 218: 365-378.*
Office Action regarding European Application No. 10 002 779.6-1501, dated Oct. 5, 2016.

\* cited by examiner

*Primary Examiner* — Yong Pak
(74) *Attorney, Agent, or Firm* — Stephen T. Olson; Harness, Dickey & Pierce, P.L.C.

(57) ABSTRACT

The present invention relates to the production of optically pure secondary amines, which can be used as intermediate products in a synthesis of for instance pharmaceutical products.

28 Claims, 11 Drawing Sheets

PROCESS FOR THE PREPARATION OF OPTICALLY ACTIVE CHIRAL AMINES

CROSS-REFERENCE TO RELATED APPLICATIONS

This application is a divisional of U.S. patent application Ser. No. 12/223,730 filed 7 Aug. 2008, which is the national phase filing of PCT/EP2007/001222 filed 13 Feb. 2007, which claims priority to EP 06002859.4 filed 13 Feb. 2006. The entire disclosures of each of the above applications are incorporated herein by reference.

The present invention relates to a process for the preparation of optically active chiral amines.

Chiral amines play an important role in the pharmaceutical, agrochemical and chemical industry. They are frequently used as intermediates or synthons for the preparation of various physiologically, for instance pharmaceutically active substances, such as cephalosporine or pyrrolidine derivatives. In a great number of the various applications of chiral amines, only one particular optically active form, either the (R) or the (S) enantiomer has the desired physiological activity. Thus, there is a clear need to provide processes for the preparation of chiral amines in an optically active form.

These needs are partially met by preparing chiral amines by crystallisation of diastereomeric salts through adding of chiral carboxylic acids (Breuer et al., Angewandte Chemie (2004) 116, 806-843). Other chemical methods use enantioselective synthesis by reducing prochiral precursors with C=N-double bonds.

Furthermore, it is known to stereoselectively cleave racemates using various enzymes, such as proteases, amidases or lipases (Bornscheuer and Kazlauskas, Hydrolases in Organic Synthesis (2005), Wiley-VCH Weinheim). It is also known that specific transaminases, namely α-transaminases including α-amino acid aminotransferases, are suitable for the preparation of optically pure amino acids (Bartsch et al., Appl. Environm. Microbiol. (1996) 62, 3794-3799, Cho et al., Biotechnol. Bioeng. (2003) 83, 226-234, JP 011 53084 A2 (1998), JP 633 04986 A2 (1988), EP 0 248 357 A2 and Ziehr et al., Biotechnol. Bioeng. (1987) 29, 482-487).

However, these prior art processes suffer from various disadvantages. Although the enzymatic processes usually employ in contrast to the classical methods favourable mild conditions and achieve a reasonable stereoselectivity, they regularly use enzymes, whose substrate specificity, enantioselectivity and/or conversion rates are not sufficiently high for industrially applicable processes. Furthermore, one of the most prominent drawbacks of using transaminases for the preparation of optically active amines is represented by the frequently observed substrate and product inhibition phenomena. It is therefore one of the objects of the present invention to provide an improved process for preparing optically active chiral amines, in particular a process with an improved substrate specificity, an improved enantioselectivity and in particular enabling a conversion of the educts of up to 100%.

The present invention solves the technical problem underlying the present invention by the provision of a process for the preparation of an optically active chiral amine comprising a) providing an amino acceptor and an amino donor, b) reacting the amino acceptor and the amino donor with a transaminase, in particular (R)- or (S)-selective transaminase and c) obtaining the desired optically active chiral amine and an α-ketone by-product. According to a preferred embodiment of the present invention, in a subsequent further optional process step, the optically active chiral amine obtained in step c) is isolated and purified from the reaction mixture obtained in step c).

The reaction of the present invention follows in principle the following scheme:

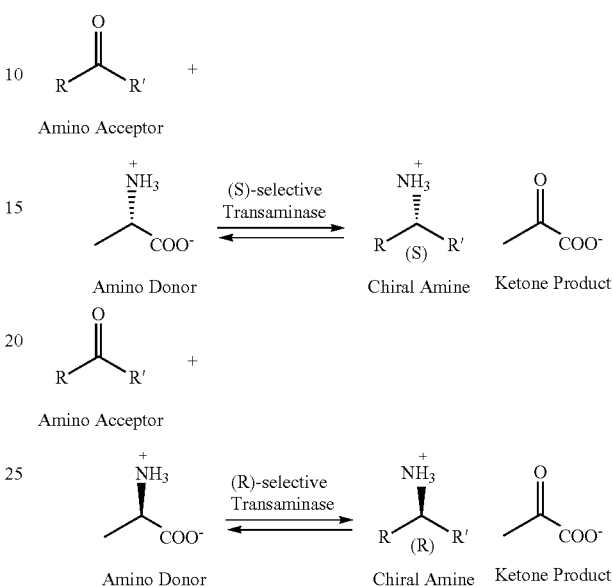

Thus, the present invention provides a process for the asymmetric synthesis of chiral amines by using at least one transaminase for the transamination of an amino group from an amino donor to an amino acceptor, thereby forming the desired product. Depending on the enantiopreference of the specific transaminase used, an optically active chiral amine of the desired optical configuration, i.e. either the (R) or (S) enantiomer, is obtained. Thus, using in one embodiment of the present invention a (S)-selective-transaminase for the asymmetric synthesis generates the desired (S) enantiomer of the chiral amine while using in another embodiment of the present invention an (R)-selective-transaminase generates the desired (R)-enantiomer. In addition to the desired optically active amine, the reaction results in a ketone by-product, in particular an α-ketone by-product, from the used amino donor and possibly non-converted amino acceptor and amino donor.

In the context of the present invention, a transaminase is a pyridoxalphosphate-dependent enzyme catalysing the transfer of amino groups. Transaminases are classified in E.C. 2.6.1.X. In a particularly preferred embodiment of the present invention, the transaminase is a (R)- or (S)-selective transaminase, particularly is in a preferred embodiment an ω-transaminase.

In the context of the present invention a ω-transaminase is an enzyme preferably with the classification code E.C.2.6.1.18. These amino transaminases are characterised in that they mainly use amines as substrates. These enzymes are further characterised by exhibiting an equilibrium constant of ω-transaminase catalysed reactions which is greater than 1. ω-transaminases which may be used according to the present invention are described for instance in Iwasaki et al., Biotechnol. Lett. (2003) 25, 1843-1846, Shin et al., Biotechnol. Bioeng. (1997) 55, 348-358, Shin and Kim, Book of Abstracts, 217th ACS National Meeting, Anaheim, Calif., March 21-25, (1999) 180, Shin and Kim, Biosc. Biotechnol.

Biochem. (2001) 65, 1782-1788 and Shin and Kim, Biotechnol. Bioeng. (1998) 60, 534-540.

Thus, in a preferred embodiment of the present invention, the transaminase, in particular the ω-transaminase used in the present process is a transaminase, in particular an ω-transaminase obtained from *Vibrio fluvialis*, in particular from strain JS17. In a further preferred embodiment, the transaminase is from *Alcaligenes denitrificans*, in particular from strain Y2k-2. In a further preferred embodiment the transaminase is from *Klebsiella pneumoniae*, in particular from strain YS2F. In a further preferred embodiment the transaminase is from *Bacillus thuringiensis*, in particular from strain JS64. For the strain designations see Shin and Kim, 1998, above. Of course the present invention also understands under the term transaminase, in particular ω-transaminase, an extract of an organism, such as a microorganism or a cell, containing a transaminase, in particular an ω-transaminase, or a living or dead cell or microorganism itself comprising a transaminase, in particular an ω-transaminase. Such a microorganism or cell or extract or transaminase enzyme may be used in immobilised or non-immobilised form. The transaminase, in particular the ω-transaminase, may also be a recombinantly produced naturally occurring or genetically modified transaminase, in particular an ω-transaminase, which is coded partially or completely by a nucleic acid sequence or a derivative thereof contained in one of the above-identified organisms or being equivalent thereto.

In the context of the present invention the term optically active chiral amine relates to the same subject-matter as the term enantiomerically active chiral amine. These terms in particular refer to a preparation which is essentially free, in an even more preferred embodiment free of the undesired enantiomer. Accordingly, an optically active chiral amine essentially comprises an excess of one enantiomer or even consists of only one enantiomer.

In particular, in the context of the present invention, an optically active chiral amine has an optical purity of at least 70%, in particular more than 90% and at best >99%.

In the present invention the optical purity is given in % excess of one enantiomer over the other enantiomer. Thus, the optical purity in is the quotient of the difference between the (R) and the (S) enantiomer concentrations and the sum of the concentrations of both enantiomers (optical purity of A in %=([A]−[B]):([A]+[B])×100, wherein A and B represent the concentrations of the (R) and (S) enantiomers or vice versa).

In the present invention it is preferred that the amino acceptor is converted to the desired chiral amine in a conversion of at least 40, 50, 60, 70, 80, 90, 95, in particular 100%. The concentrations for analysing the optical purity and the conversion can be determined for instance using gaschromatography (GC) or photo- or fluori metric methods.

In the context of the present invention an amino acceptor is a molecule capable of accepting an amino group transferred from an amino donor by a transaminase, in particular an ω-transaminase. In a particularly preferred embodiment of the present invention the amino acceptor contains a ketone functionality. In a particularly preferred embodiment of the present invention the amino acceptor is selected from the group consisting of phenylpyruvic acid, a salt thereof, pyruvic acid, a salt thereof, acetophenone, 2-ketoglutarate, 3-oxobutyrate, 2-butanone, 3-oxopyrrolidine (3-OP), 3-pyridylmethylketone (3-PMK), 3-oxobutyric acid ethyl ester (3-OBEE), 3-oxopentanoic acid methyl ester (3-OPME), N-1-boc-3-oxopiperidinone, N-1-boc-3-oxopyrrolidine (B3OP), 3-oxo-piperidine, alkyl-3-oxo-butonoates, methoxyacetone and 1-oxotetralone.

In a particularly preferred embodiment the amino acceptor is B3OP.

In the context of the present invention an amino donor is a molecule capable of providing an amino group to an amino acceptor using a transaminase, in particular an ω-transaminase. In a particular preferred embodiment the amino donor is an amine or amino acid.

In a particularly preferred embodiment the amino donor is selected from the group consisting of β-alanine, alanine, in particular D,L-alanine, L-alanine or D-alanine, α-methylbenzylamine (α-MBA), glutamate, phenylalanine, glycin, 3-aminobutyrate, isopropylamine, 2-aminobutane, γ-aminobutyrate and a salt, for instance a chloride, of any one thereof. In a particularly preferred embodiment the obtained ketone product may be phenylpyruvic acid, a salt thereof, pyruvic acid, a salt thereof, glyoxylic acid, a salt thereof, acetophenone, 2-ketoglutarate, acetone, 3-oxobutyrate, 2-butanone, 3-oxopyrrolidine (3-OP), 3-pyridylmethylketone (3-PMK), 3-oxobutyric acid ethyl ester (3-OBEE), 3-oxopentanoic acid methyl ester (3-OPME), N-1-boc-3-oxopiperidinone and N-1-boc-3-oxopyrrolidine (B3OP) or a salt, for instance a chloride, of any one thereof.

In a particularly preferred embodiment the amino donor is alanine, in particular L-alanine.

In a further preferred embodiment the present invention relates to a process for the preparation of an optically active chiral amine which is selected from the group of amines having an optically active amino group, in particular amines with alkylgroups, branched alkylgroups or arylalkylgroups. In particular, these amines, in particular mono- or bicyclic amines, are in particular amines of 5 to 6-membered cyclic or S-, O-, or N-substituted heterocyclic hydrocarbons or aromatic amines, in particular alkyl- or alkoxy-substituted aromatic amines. In a preferred embodiment, the obtained chiral amines are selected from the group consisting of phenylalanine, alanine, 3-aminopiperidine, alkyl-3-aminobutanoates, 3-aminopyrrolidine (3-AP), 3-pyridyl-1-ethylamine (3-PEA), N-1-boc-3-aminopyrrolidine (B3AP), 3-aminobutyric acid ethyl ester (3-ABEE), 3-aminopentanoic acid methyl ester (3-APME), α-methylbenzylamine (α-MBA), 1-aminotetraline, α-methyl-4-(3-pyridyl)-butanamine, glutamate, β-aminobutyrate, sec-butylamine, methoxyisopropylamine, derivatives of 3-aminopyrrolidine, 1-N-Boc-3-aminopiperidin, cephalosporine and derivatives of cephalosporine.

In a particularly preferred embodiment the present invention therefore foresees reacting 3OP with an (S)- or (R)-selective transaminase and an amino donor to obtain optically active (S) or (R)-3AP.

In a further preferred embodiment, the present invention foresees reacting 3-PMK with an (R)- or (S)-selective transaminase and an amino donor to obtain optically active (R) or (S) 3-PEA.

In a further preferred embodiment of the present invention, the invention foresees reacting 3-OBEE with an (R)- or (S)-selective transaminase and an amino donor to obtain optically active (R) or (S) 3-ABEE.

In a further preferred embodiment the invention foresees reacting 3-OPME with an (R)- or (S)-selective transaminase and an amino donor to obtain optically active (R) or (S) 3-APME.

In a further preferred embodiment the invention foresees reacting B3OP with an (R)- or (S)-selective transaminase and an amino donor, in particular alanine, to obtain optically active (R) or (S) B3AP.

In a particularly preferred embodiment the invention relates to a reaction between B3OP and an amino donor, in particular alanine, in the presence of a transaminase to obtain optically active B3AP and pyruvate, wherein the reaction is carried out at a pH from 5.0 to 9.5, preferably 6.0 to 7.0, in particular 6.0 to 6.9, for a time from 30 to 70 minutes, in particular 40 to 65 minutes, in particular 50 to 60 minutes.

In a particularly preferred embodiment said transaminase is an (R)-selective transaminase. In a further preferred embodiment said transaminase is an (S)-selective transaminase.

In a preferred embodiment, said reaction of B3OP with the amino donor, in particular alanine, is carried out in the presence of at least one pyruvate decarboxylase (PDC). In a further preferred embodiment said reaction of B3OP with the amino donor, in particular alanine, in the presence of at least one pyruvate decarboxylase, is carried out while simultaneously introducing gaseous nitrogen in the reaction mixture for the removal of the acetaldehyde obtained from the formed pyruvate by the action of the PDC.

In a further preferred embodiment said reaction of B3OP with the amino donor, in particular alanine, in the presence of at least one pyruvate decarboxylase is carried out in the presence of at least one alcohol dehydrogenase (ADH) for the removal of the acetaldehyde obtained from the formed pyruvate by the action of the PDC.

In a further preferred embodiment said reaction of B3OP with the amino donor, in particular alanine, in the presence of at least one pyruvate decarboxylase is carried out while simultaneously introducing gaseous nitrogen into the reaction mixture, wherein at least one alcohol dehydrogenase is present in the reaction medium to remove the acetaldehyde obtained from the formed pyruvate by the action of the PDC.

In a further preferred embodiment of the present invention the invention foresees reacting acetophenone with an (R) or (S)-selective transaminase and an amino donor to obtain optically active (R) or (S) α-MBA.

In a further preferred embodiment the present invention foresees reacting as an amino acceptor, in particular mono- or bicyclic, oxogroup-containing 5 to 6 membered cyclic or S-, O-, or N-substituted heterocyclic hydrocarbons or aromatics, in particular alkyl- or alkoxy-substituted aromatics with an amino donor and an (R) or (S)-selective transaminase to obtain optically active amines, in particular mono- or bicyclic amines, in particular amines of 5 to 6 membered cyclic or S-, O-, or N-substituted heterocyclic hydrocarbons or aromatic amines, in particular alkyl- or alkoxy-substituted aromatic amines, in particular in (S) or (R) form.

In a particularly preferred embodiment of the present invention, the amino acceptor and the amino donor are reacted with the transaminase in aqueous medium, for example physiological buffer. In a particularly preferred embodiment the transamination reaction is carried out at a pH in the range from 5.0 to 9.5 or 5.0 to 9.0, in particular from 7 to 8.5. The invention foresees in a particularly preferred embodiment to react the amino acceptor and the amino donor at a pH-value from 6.0 to 7.0, preferably from 6.0 to 6.9.

In a particular preferred embodiment, the reaction is carried out in a temperature range from 10 to 65° C., preferably 20 to 50° C., in particular 18 to 25° C., preferably room temperature or 34° C. to 39° C., in particular 37° C. In a further preferred embodiment of the present invention the amino acceptor and the amino donor are provided in a molar ratio from 1:50 to 1:200, in particular from 1:50 to 1:100, in particular 1:100, in particular from 1:1 to 1:5, in particular from 1:1 to 1:2. In a preferred embodiment of the present invention the enzymatic activity may be from 1 to 20.000 μmol/min.

In a further preferred embodiment the reaction is carried out for a reaction time of 30 to 70, preferably 40 to 65, in particular 50 to 60 minutes.

In a particularly preferred embodiment, the present invention relates to a process for the preparation of an optically active chiral amine according to the above, that means according to which in a first process step a) an amino acceptor and an amino donor are provided, in a second process step b) the amino acceptor and the amino donor are reacted with at least one .omega.-transaminase, in a third process step c) an optically pure chiral amine and an .alpha.-ketone by-product are obtained, and wherein in a further process step d) the ketone by-product, in particular the .alpha.-ketone by-product, obtained in step c) is removed from the obtained reaction mixture, in particular removed by reaction with an enzyme, that means by enzymatic cleavage, in particular using an enzyme selected from the group consisting of a decarboxylase, a synthase, a synthetase or a dehydrogenase.

In a particularly preferred embodiment, the ketone product, in particular pyruvate, obtained in step c) is removed by reaction with a pyruvate decarboxylase (PDC), for instance from *Saccharomyces cerevisiae*, *Zymomonas mobilis* or *Zymobacter palmae*, thereby preferably producing acetaldehyde and $CO_2$.

In a further preferred embodiment the invention relates to a process, wherein the ketone product obtained, in particular pyruvate, is removed by action of a PDC and wherein the acetaldehyde formed thereby is removed for instance by a chemical, enzymatic or physical treatment.

In a further preferred embodiment the invention relates to a process, wherein the ketone product obtained, in particular pyruvate, is removed by action of a PDC and wherein the acetaldehyde formed thereby is removed for instance by feeding gaseous nitrogen into the reaction mixture, preferably by feeding said gaseous nitrogen continuously into the reaction mixture, to remove the acetaldehyde from the reaction mixture.

In a further preferred embodiment the invention relates to a process, wherein the ketone product obtained, in particular pyruvate, is removed by action of a PDC and wherein the acetaldehyde formed thereby is removed by reacting the acetaldehyde with at least one alcohol dehydroxygenase (ADH) to remove the acetaldehyde from the reaction mixture and convert it to ethanol.

In a further preferred embodiment the invention relates to a process, wherein the ketone product obtained, in particular pyruvate, is removed by action of a PDC and wherein the acetaldehyde formed thereby is removed by applying a reduced pressure to the reaction mixture.

In a further preferred embodiment the invention relates to a process, wherein the ketone product obtained, in particular pyruvate, is removed by action of a PDC and wherein the acetaldehyde formed thereby is removed by chemical reactions.

In a further preferred embodiment the invention relates to a process, wherein the ketone product obtained, in particular pyruvate, is removed by action of a PDC and wherein the acetaldehyde formed thereby is removed by feeding gaseous nitrogen into the reaction mixture, preferably by feeding said gaseous nitrogen continuously into the reaction mixture, and wherein additionally the acetaldehyde is reacted with at least one alcohol dehydroxygenase (ADH) to remove the acetaldehyde from the reaction mixture and convert it to ethanol.

In a further preferred embodiment, the ketone product, in particular pyruvate, obtained in step c) is removed by reaction with a lactate dehydrogenase (LDH), for instance from *Escherichia coli*, thereby preferably producing L-lactate.

In a further preferred embodiment the ketone product, in particular pyruvate, obtained in step c) is removed by reaction with an acetolactase synthase, thereby preferably producing acetolactate.

In a further preferred embodiment of the present invention the ketone product, in particular pyruvate, obtained in step c) is continuously removed from the reaction mixture.

These particularly preferred embodiments provide the advantage of obtaining a particularly high conversion rate, since the ketone product as by-product of the present process is removed from the equilibrium reaction. The reaction is forced in direction of the products, thereby providing with a high stereoselectivity a very high conversion into the desired products.

The present invention also relates to processes for the preparation of physiologically active compounds or their precursors and/or intermediates in the production thereof, in particular selected from the group of 3-aminopyrrolidine derivatives, cephalosporine, derivatives of cephalosporine, heterocyclic boronic acids, L-dihydroxyphenylalanine (L-Dopa), α-methyldopa, D-phenylglycine, β-hydroxyphenylglycine, phosphinothricine, pyrimido derivatives and pyrrolidone derivatives, wherein any one of the above identified processes of the present invention is employed. In the context of the present invention, a physiologically active compound is a compound which is physiologically active either in plants, animals, humans, yeasts or microorganisms, such as protozoa, bacteria or viruses, i.e. interacts with the metabolism of the organism.

Further preferred embodiments of the present invention are the subject matter of subclaims.

The present invention is illustrated in more detail in the following examples and the accompanying figures.

The accompanying figures illustrate the present invention.

EXAMPLE 1

Asymmetric Synthesis of B3AP

Figure 1:
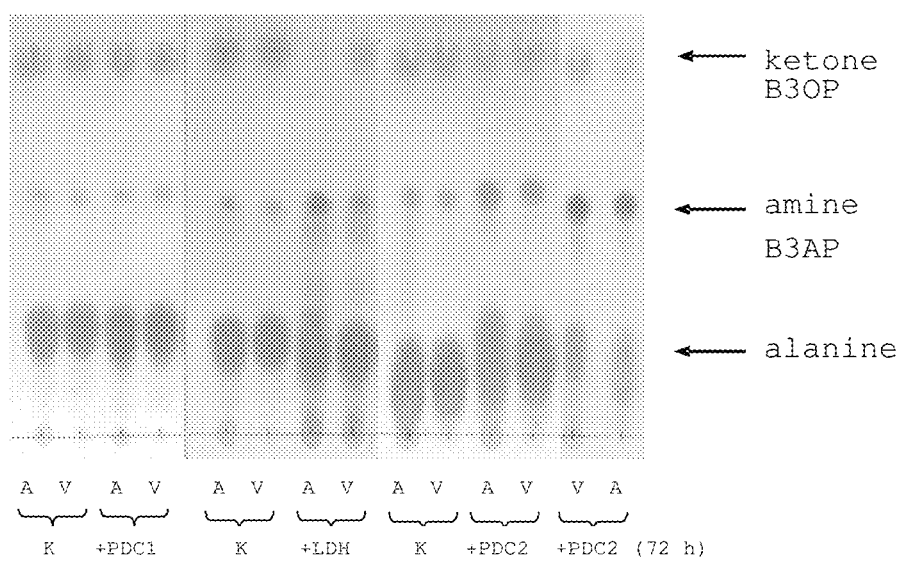
FIG. 1 shows a thin layer chromatogramm.

The asymmetric synthesis of B3AP was carried out in 1.5 ml reaction tubes. B3OP as amino acceptor was used in a concentration of 5 mM (7.5 µmol). The concentration of the used amino donor L-alanine was 5 mM. The reagents and reaction conditions used are evident from table 1 below.

TABLE 1

Reaction conditions for the asymmetric (S)-B3AP synthesis using (S)-ω transaminase for transaminating the amino group from alanine to B3OP

|  | 1 | | 2 | | 3 | 4 | | 5 | | 6 | |
|---|---|---|---|---|---|---|---|---|---|---|---|
| B3OP, 20 mM [µl] | 375 | | 375 | | 375 | 375 | | 375 | | 375 | |
| D,L-Ala, 100 mM [µl] | 150 | | 26 mg D,L-Ala | | 150 | 150 | | 150 | | 150 | |
| TA7/TA8 [µl] | 18 | 111 | 18 | 111 | 111 | 18 | 111 | 18 | 111 | 18 | 111 |
| LDH [µl] | — | | — | | — | — | | — | | 500 µl + 60 µl 250 mM NADH | |
| PDC1 [µl] | — | | — | | 200 (15 U) | — | | — | | — | |
| PDC2 [µl] | — | | — | | — | 34 (20 U) | | 34 (20 U) | | — | |
| Buffer [µl] | 957 | 864 | 1218 | 1125 | 664 | 923 | 830 | 923 | 830 | 397 | 304 |

The buffer used was 50 mM sodium phosphate, pH 7. TA7 designates the ω-transaminase from *Vibrio fluvialis* (Jülich Fine Chemicals, Germany). TA8 designates the ω transaminase from *Alcaligenes denitrificans* (Jülich Fine Chemicals, Germany). As lactate dehydrogenase an extract of *Escherichia coli* was used. In addition, NADH was added to a final concentration of 10 mM. The concentration of pyruvate decarboxylase was varied. 1.5 units (20 µl) and 15 units (200 µl) of the pyruvate decarboxylase of *Saccharomyces cerevisiae* (PDC1) were used. 2 units (3.4 µl) and 20 units (34 µl) of the pyruvate decarboxylase of *Zymomonas mobilis* (PDC2) were used.

TABLE 2

Conversion and optical purity obtained using TA8 for the asymmetric synthesis of B3AP. The calculations were based on GC-analysis (+/−5%)

| Run | Enzyme | Conversion [%] | % $ee_s$ [%] (S)-enantiomer |
|---|---|---|---|
| 1 | TA7 or TA8 alone | 1.3 | 99.4 |
| 2 | Excess of Alanine (50-fold) | 10.1 | 99.6 |
| 3 | PDC *Saccharomyces cerevisiae* | 4.6 | 99.5 |
| 4 | PDC *Zymomonas mobilis* | 34.0 | 99.6 |

TABLE 2-continued

Conversion and optical purity obtained using TA8 for the asymmetric synthesis of B3AP. The calculations were based on GC-analysis (+/−5%)

| Run | Enzyme | Conversion [%] | % ee$_s$ [%] (S)-enantiomer |
|---|---|---|---|
| 5 | PDC *Zymomonas mobilis* (72 hrs) | 73.0 | 99.4 |
| 6 | LDH *Escherichia coli* | 66.5 | 99.9 |

Referring now to table 2, above, it is evident that in each of the six runs using the ω-transaminase TA8, a very high degree of optical purity for the obtained (S)-B3AP could be achieved. It was also observed that independently from using either TA7 or TA8 the degree of conversion was only moderate, if the equilibrium of the reaction was not influenced (run 1). Using alanine in a 10-50-fold excess only slightly improved the conversion. In runs 3, 4, 5 and 6 the ketone product of the reaction, that means pyruvate, was, during the transamination reaction, removed from the equilibrium reaction. The use of TA8 together with lactate dehydrogenase from *E. coli* (run 6) led to an extremely improved degree of conversion while maintaining and even improving the enantioselectivity. Essentially the same holds valid for the enantioselectivity provided by the pyruvate decarboxylase from *Zymomonas mobilis* (runs 3 to 5). PDC1, however, only slightly increased the conversion, PDC2 moderately increased the conversion rate (run 4) if reacted for 24 hrs while in a 72 hr reaction (run 5) the conversion was drastically improved. All the reactions took place for 24 hrs except for run 5, which took place for 72 hrs.

The figure shows the thin layer chromatogram of reactions carried out according to table 1. "A" designates the ω-transaminase from *Alcaligenis denitrificans* while "V" the ω-transaminase from *Vibrio fluvialis*. "K" designates run 1 using TA7 or TA8 alone (run 1). PDC1 designates the run with *Saccharomyces cerevisiae* pyruvate decarboxylase (run 3), LDH the run with lactate dehydrogenase from *Escherichia coli* (run 6) and PDC2 the run with *Zymomonas mobilis* pyruvate decarboxylase (after 24 and 72 hrs) (run 4 and 5). Thus, the results clearly show that the production of (S)-B3AP from the prochiral ketone B3OP could be carried out with a very high enantioselectivity. Using the ω-transaminases as the sole enzymes in the preparation process, however, leads to a moderate conversion. This moderate conversion rate could be greatly improved by removing pyruvate from the equilibrium, in particular using lactate dehydrogenase or pyruvate decarboxylase. Using pyruvate decarboxylase has inter alia the advantage that no co-factor recycling (NADH) was necessary. It further advantageously provides the enzymatic removal of pyruvate with PDC and thereby provides the additional advantage of removing or avoiding product inhibition (product ketone) and pulling the reaction equilibrium to the right achieving higher conversion (ideal case 100%).

Figure 2:
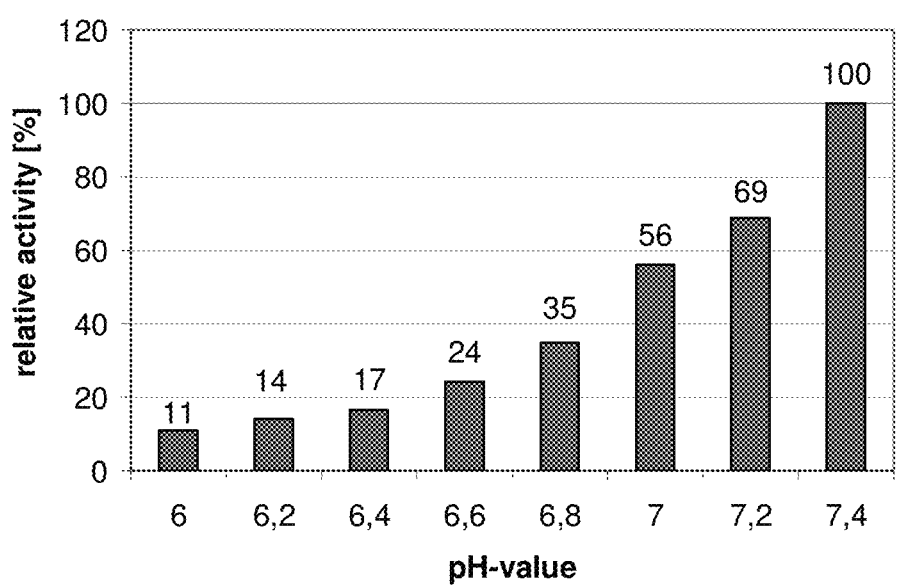
FIG. 2 shows the relative activity of *V. fluvialis* ω-TA in dependence from the pH-value.

EXAMPLE 2 pH-Dependency of ω-Transaminase Activity in the Conversion Reaction of (S)-αMBA to Acetophenone The synthesis was carried out in a quarz cuvette using 50 μl 100 mM pyruvate, 4 units/ml of ω-TA *Vibrio fluvialis* (in the following also Vfl) (12 μl) and 388 μl of sodium phosphate buffer, 50 mM with pH-variations from pH 6.0 to pH 7.4 in 0.2 steps. The reaction was started with 50 μl 100 mM (S)-αMBA as amino donor and the increase in absorption was measured at 250 to 260 nm. The increase in absorption is due to the acetophenone formed. The other substrates only insignificantly contribute to the absorption so that the velocity of the reaction can be determined by measuring the absorption of acetophenone. The value reached at pH 7.4 was set as 100% and the relative activity for the other pH-values was calculated as is evident from FIG. 2. FIG. 2 shows the relative activity of *V. fluvialis* ω-TA in dependence from the given pH-value.

FIG. 2 shows that at lower pH-values such as 6.0, 6.2 or 6.4 there is still considerable activity present, for instance 11% at pH 6.0. Thus, this result demonstrates that even at a low pH, it is possible to obtain a significant transaminase activity, allowing to react the substrates at a lower pH, which in turn allows to increase the conversion by using a PDC, which is sensitive to higher pH-values.

EXAMPLE 3

Asymmetric Synthesis of B3AP at Different pH-Values

In this example, the asymmetric synthesis of B3AP from alanine and B3OP is shown in the presence and absence of a pyruvate decarboxylase (PDC).

For each pH-value 6.0, 6.4 and 7.0 three runs of experiments were conducted. Run 1 used the PDC of *Zymomonas mobilis* (wild-type cell extract), run 2 used the *Zymobacter palmae* (recombinant in *E. coli*) and run 3 was a control without PDC, employing only the transaminase. To obtain comparable results, the activities of both of the PDC's have been determined at pH 6 with an alcohol dehydrogenase assay and the same quantity of activity of the PDC's was used in the runs identified above.

Table 3 gives the volumes of the used substance in μl. Each reaction run was carried out three times at pH-values 6.0, 6.4 and 7.0. The pH-value was adjusted by the buffer of the B3OP substrate solution. The activity of the PDC was about 2.5 units/ml at pH 7. The substrate and enzyme concentrations are also evident from table 3 below. After 10 minutes, 30 minutes, 60 minutes and 120 minutes a sample of 100 μl was taken and the reaction stopped by the addition of 100 μl 1 M NaOH. The quantification of the B3AP-concentration was done using CE (capillary electrophoresis).

TABLE 3

|  | Run 1 | Run 2 | Run 3 |
|---|---|---|---|
| 10 mM B3OP in 100 mM buffer of corresponding pH-value | 500 | 500 | 500 |
| 400 mM D,L-alanine | 25 | 25 | 25 |
| PDC *Z. mobilis* | 290 | — | — |
| PDC *Zb. palmae* | — | 18.32 | — |
| *V. fluvialis* ω-TA at pH 7.0 | 21.4 | 21.4 | 21.4 |
| *V. fluvialis* ω-TA at pH 6.4 | 72.3 | 72.3 | 72.3 |
| *V. fluvialis* ω-TA at pH 6.0 | 110 | 110 | 110 |
| 4 mM TPP | 25 | 25 | 25 |
| 4 mM PLP | 25 | 25 | 25 |
| 40 mM MgCl$_2$ | 25 | 25 | 25 |
| Water | | ad 1000 μl | |

Table 4 below shows the conversion at different pH-values for the different PDC's. It is evident that the use of the PDC increases the conversion. It is also evident that the PDC from Z. palmae (Zpa) causes a somewhat higher conversion than the PDC from Z. mobilis (Zmo). It is also evident that at lower pH-values, such as 6.0 or 6.4, a remarkable conversion increase in the runs employing PDC's is to be observed, which is not to be seen in the PDC-free control. In all reaction runs it could be observed that after 120 minutes the conversion decreased.

TABLE 4

| | Conversion | | | | | | | | |
|---|---|---|---|---|---|---|---|---|---|
| | Run 1 (Zmo) | | | Run 2 (Zpa) | | | Run 3 (control) | | |
| Time (min) | pH 6 | pH 6.4 | pH 7 | pH 6 | pH 6.4 | pH 7 | pH 6 | pH 6.4 | pH 7 |
| 10 | 7.5 | 5.5 | 2.4 | 12.1 | 9.8 | 4.9 | 2.5 | 2.4 | 2.0 |
| 30 | 11.4 | 14.2 | 9.6 | 16.0 | 17.8 | 15.2 | 5.1 | 4.8 | 4.6 |
| 60 | 8.3 | n.d. | 12.4 | 11.0 | n.d. | 16.3 | 7.0 | n.d. | n.d. | n.d. = not determined

EXAMPLE 4

Stability of B3AP in the Presence of Various Reactants of an Asymmetric Synthesis Reaction To show the stability of B3AP in the presence of various reactants incubations of 1 mM B3AP were conducted in a reaction tube for 3 hrs in the presence of various substances as listed in table 5 below.

The example was carried out at a pH of 6 and 7 (sodium phosphate buffer). Directly after reacting the substances being a first sample $T_0$ was taken, and another sample, $T_1$, after 3 hrs. After the extraction the amine concentration was determined with an internal standard (αMBA) by CE. From the difference of the concentrations obtained, the %-decrease of the B3AP concentration was calculated (see FIG. 3).

TABLE 5

| Run | 1 mM B3AP and: Reactants |
|---|---|
| 1 | 50 mM Na-P-buffer |
| 2 | 5 mM B3OP |
| 3 | 10 mM D,L-alanin |
| 4 | cofactors (0.1 mM PLP, TPP, 5 mM Mg) |
| 5 | cofactors + B3OP + alanine |
| 6 | 145 μl Z. mobilis cell extract (50% glycerine) |
| 7 | 10 μl E.coli cell extract (Zpa PDC recombinant) |
| 8 | 55 μl/11 μl Vfl-TA (pH6/7) |
| 9 | 50 μl Ade-TA |
| 10 | Vfl-TA + B3OP + cofactors |
| 11 | 1 mM acetaldehyde |
| 12 | Vfl-TA + acetaldehyde |
| 13 | Ade-TA + acetaldehyde |

Figure 3:
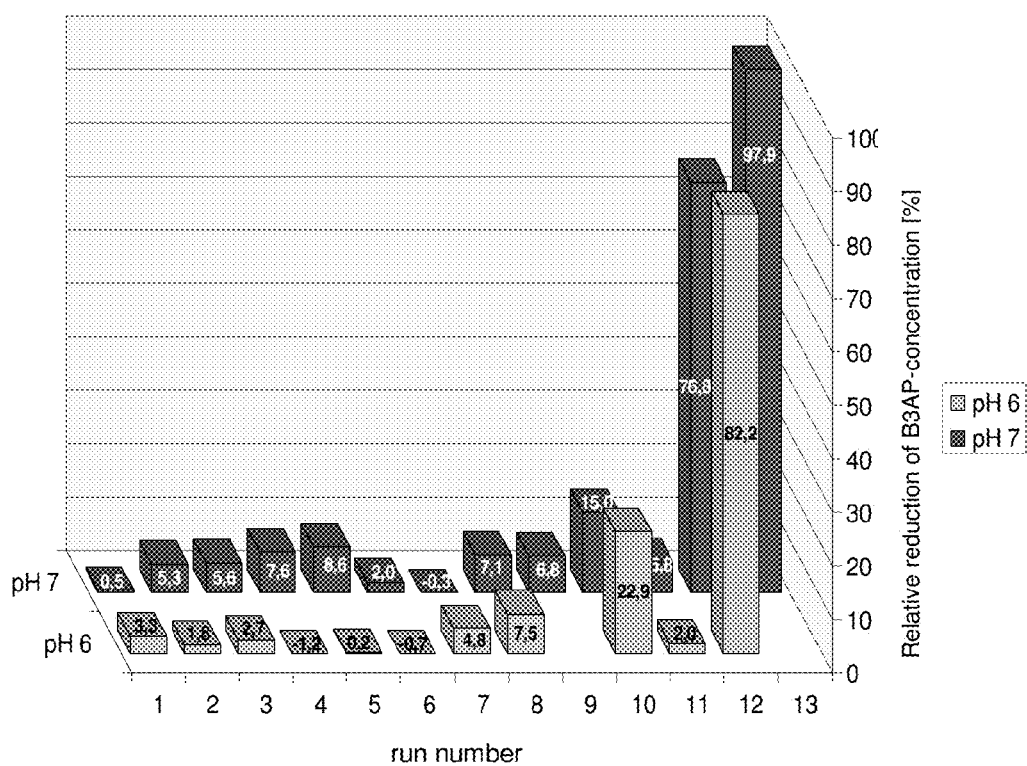
FIG. 3 shows the relative reduction of the B3AP concentration for incubations with various substances.

From FIG. 3 it is evident that the different reactants do not significantly affect the B3AP-concentration (runs 1 to 9). Reaction runs 11 to 13 show the influence of acetaldehyde. From run 11 it is evident that in the absence of a transaminase there is no reduction in the B3AP concentration, while in the presence of a transaminase and acetaldehyde a strong reduction in B3AP-concentration can be observed. Acetaldehyde functions in the transaminase reaction as an amino acceptor, such as pyruvate, and obviously leads to a reduction in B3AP concentration.

EXAMPLE 5

Reaction of B3AP with the Amino Acceptors Pyruvate and Acetaldehyde

In this example the transaminase activity of V. fluvialis and A. denitrificans ω-TA for the substrates B3AP and pyruvate and for B3AP and acetaldehyde is shown.

Figure 4:
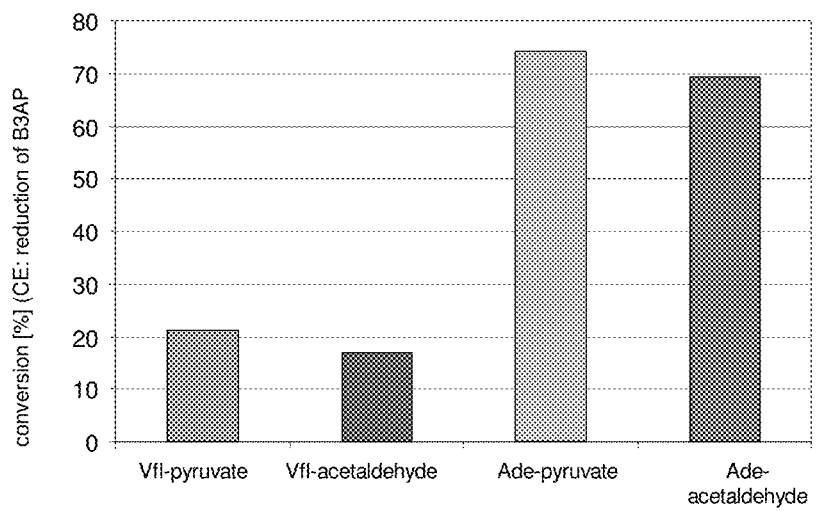
FIG. 4 shows the relative reduction of the B3AP conversion in the presence of pyruvate and acetaldehyde.

2 mM B3AP was reacted with 2 mM pyruvate or 2 mM acetaldehyde (36 μl Alcaligenes denitrificans (Ade) or 6 μl Vibrio fluvialis (Vfl)-transaminase per 0.5 μl reaction volume, corresponding to 2 units/μl transaminase was reacted for 30 minutes). FIG. 4 shows the results. Accordingly, B3AP was converted to B3OP by both enzymes, both with pyruvate and acetaldehyde, without any significant differences.

EXAMPLE 6

Asymmetric Synthesis of B3AP Under Reduced Pressure at pH 6

In this example, a reduced pressure was applied to the reaction mixture for an asymmetric synthesis reaction to form B3AP. As a control, the same reaction was carried out under normal pressure and without PDC.
Reaction Conditions:
Final volume: 1.5 ml
50 mM sodium phosphate buffer, pH 6
300 μl Vibrio fluvialis-transaminase
60 μl Zpa-PDC (corresponds to 8 units/ml at pH 7)
5 mM B3OP
10 mM D,L-alanine
0.1 mM TPP, PLP
5 mM $MgCl_2$ The reduced pressure was applied using a rotary evaporator (150 mBar). The measurement was done using CE.

Figure 5:
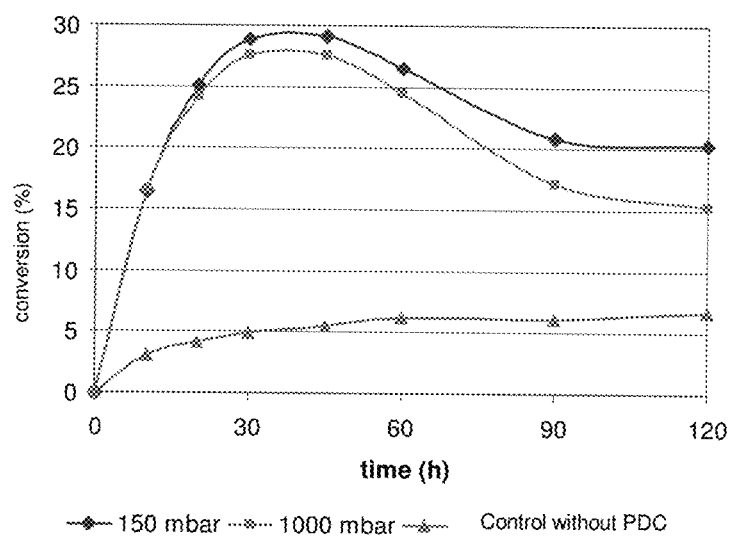
FIG. 5 shows the conversion of B3OP to B3AP over the time for various pressures.

FIG. 5 shows the conversion of B3OP to B3AP over the time for various pressures. It is evident that the conversion is almost independent from the pressure applied. The conversion at a pressure of 150 mbar is, with regard to the maximal conversion reached, similar to the conversion at a pressure of 1000 mbar.

EXAMPLE 7

Comparison of Various Pyruvate Decarboxylases

In this example, three different pyruvate decarboxylases were used for the asymmetric synthesis of B3AP. The reaction conditions correspond to those of example 6, except that a pH of 7 was used. PDC's from Z. mobilis, Z. palmae and a PDC from Biocatalytics (catalogue no. PDC-101) were used. The activities of the PDC's in the ADH-assay were identical (1.6 units/ml).

Figure 6:
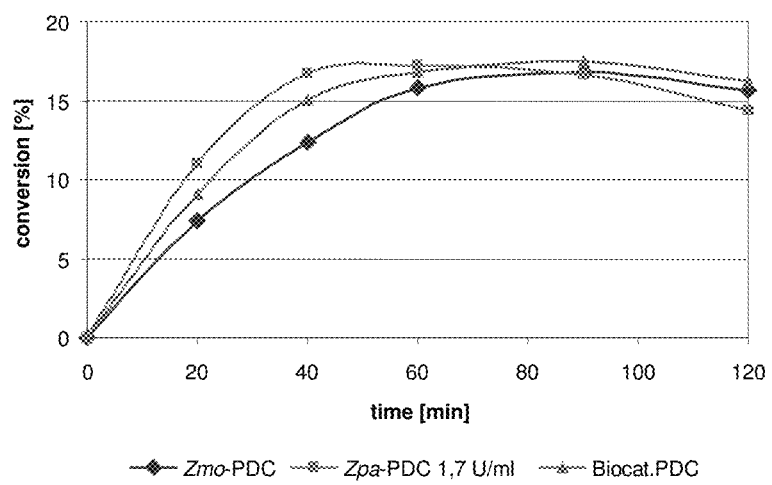
FIG. 6 shows the relative conversion of B3OP to B3AP in the presence of various PDC's.

FIG. 6 shows that all three PDC's essentially result in comparable conversions.

EXAMPLE 8

Influence of Enzyme and Co-Substrate Concentrations on the Conversion of B3OP to B3AP In this example the influence of the concentration of PDC on the conversion of B3OP to B3AP using alanine as amino donor is shown. Furthermore, the influence of the alanine concentration on the conversion of B3OP to B3AP is shown.

The reaction conditions are given in example 6, except that a pH of 7 was used and except if otherwise stated. *Zymobacter palmae* TA was used.

Figure 7:
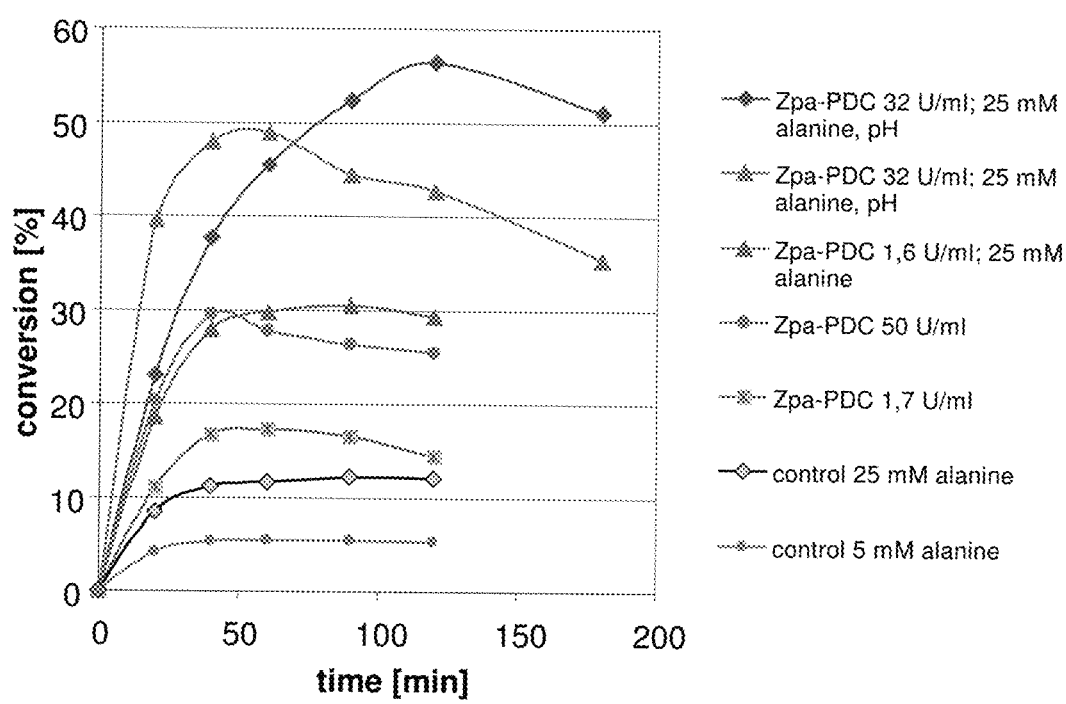
FIG. 7 shows the effect of an increased alanine concentration and an increased PDC-concentration on asymmetric B3AP synthesis.

As is evident from FIG. 7, in a reaction without PDC a 5-fold increase of the alanine concentration from 5 mM to 25 mM results in a duplication of the conversion (12% in contrast to 5.3% conversion after 2 hrs). In the presence of PDC, the conversion increases at a 5-fold alanine excess to the duplicate (30% in contrast to 17% after 90 minutes). In case the amount of PDC is increased at the usual alanine concentration from 1.6 units/ml to 50 units/ml, the conversion is also increased, however, only by a factor <2 (29% in contrast to 17% after 40 minutes).

In a further run of experiments, the influence of a combined alanine excess and a PDC excess was shown, both at a pH of 6 and 7. The reaction is faster at a pH of 6, whereas after reaching a conversion of 49%, the B3AP concentration also decreases faster. At a pH of 7 the conversion increased up to 56%.

EXAMPLE 9

Influence of the Alanine Concentration on the Asymmetric Synthesis of B3AP

In four reactions, alanine concentrations of 5 mM, 25 mM, 110 mM, 300 mM and 500 mM were used. For each run, one control without PDC and one reaction with PDC was carried out. The pH-value was adjusted to pH 7.0. Samples were taken every half hour for a reaction time of 3 hours. The reaction times for the conversions given in FIG. 8 were for 5 mM 40 minutes, for 25 mM 60 minutes and for 110 to 500 mM 90 minutes.

Figure 8:
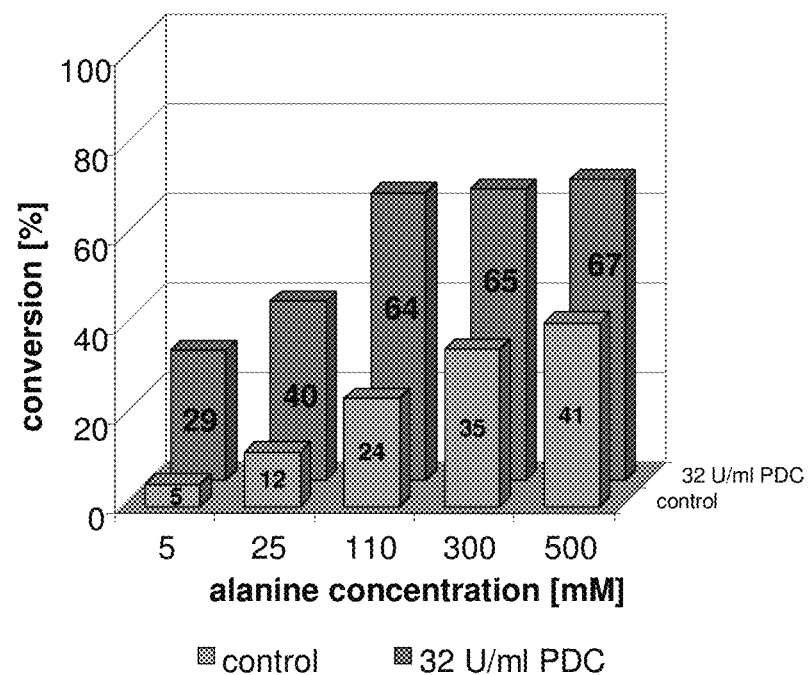
FIG. 8 shows the conversion of B3OP to B3AP at increased alanine concentrations.

FIG. 8 shows the conversion of the asymmetric B3AP-synthesis at increased alanine concentrations.

FIG. 8 clearly shows that the conversion can reach 60 to 70%. It is evident that increasing the alanine concentration from 25 to 110 mM has a significant effect on the conversion from B3OP to B3AP and that a further increase up to 500 mM only slightly influences the conversion. The influence of PDC on the conversion decreases with increasing alanine concentration.

From the data of the control reaction, the equilibrium constant of the B3AP synthesis was calculated as follows:

$$[B3AP]=[Pyr]$$

$$[B3OP]=c_{0,B3OP}-[B3AP] \text{ and}$$

$$[Ala]=c_{0,Ala}-[B3AP]$$

Thus, using the measured B3AP concentration, the equilibrium constant was calculated as:

$$K = \frac{[B3AP] \cdot [Pyr]}{[B3OP] \cdot [Ala]} = \frac{[B3AP]^2}{(c_{0,B3OP} - [B3AP]) \cdot (c_{0,Ala} - [B3AP])}$$

TABLE 6

| $c_0$, [Ala] | [B3AP] | $K \cdot 10^{-3}$ |
| --- | --- | --- |
| 5 | 5 | 3.2 |
| 25 | 12 | 3.1 |
| 110 | 24 | 3.5 |

TABLE 6-continued

| $c_0$, [Ala] | [B3AP] | $K \cdot 10^{-3}$ |
| --- | --- | --- |
| 300 | 35 | 3.2 |
| 500 | 40 | 2.8 |
| Mean of K: | | 3.1 |

Table 6 shows the calculated values. Thus the equilibrium constant for the reaction with B3AP is $3.1 \times 10^{-3}$. Thus, the substrate B3OP is a suitable substrate for the asymmetric synthesis in contrast to other ketones.

EXAMPLE 10

Influence of PLP on the Asymmetric Synthesis of B3AP

In this example, the influence of PLP (pyridoxal-5'-phosphate) on the conversion of B3OP to B3AP is shown. The following three reaction runs have been examined.
a) Run 1 using 0.1 mM PLP without addition of further PLP.
b) In run 2 PLP was added during the reaction as soon as the yellow colour, which is due to the presence of PLP in the reaction medium, has faded. For this purpose, 1 to 2 µl of a saturated PLP solution is added, thereby regaining a strong yellow colour. The influence on the amine concentration through this slight increase in volume is considered to be below 1% and can therefore be neglected.
c) No PLP present and no PLP added.

Reaction conditions: 1 ml final volume, 37 µl Vfl-transaminase, 5 mM B3OP, phosphate buffer pH 7.0. The L-alanine concentration was 110 mM. The measurements were taken by CE and α-MBA was used as internal standard.

Figure 9:
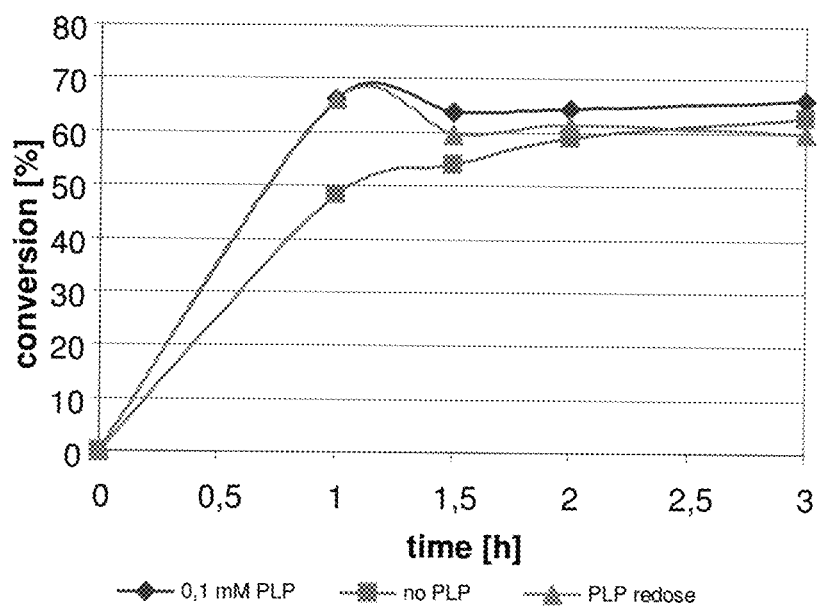
FIG. 9 shows the relative PLP-dependent conversion of B3OP to B3AP.

FIG. 9 shows the conversion over the time. There appears to be no significant influence on the maximal conversion due to the PLP addition in run b) compared to run a). The reaction without PLP appears to be slower, although it reached the same conversion as the other reactions. The addition of PLP in run b) causes a slightly greater reduction in the amine concentration as compared to the control run.

EXAMPLE 11

Asymmetric Synthesis of B3AP with Removal of Acetaldehyde by the Addition of Nitrogen The following example details one way to improve the conversion of the asymmetric synthesis of B3AP by the removal of acetaldehyde.
Reaction Conditions:
Substrates:
5 mM B3OP
500 mM L-alanine
32 U/ml Zpa-PDC
37 µl/ml Vfl-transaminase
Sodium phosphate buffer pH 7.0
0.1 mM PLP and TPP (thiamine diphosphate)
5 mM $MgCl_2$ Since the reaction solution contained a significant amount of protein, there was a strong tendency to the formation of foam. To suppress said foaming, 0.6 µl of an antifoam A concentrate (Sigma, silicone-polymer) was added to the reaction run. The concentrate suppressed the foam generation to a large extent but could not inhibit it completely. To exclude that said antifoam concentrate inhibits the enzymes, a control run without the addition of nitrogen was supplemented with antifoam A.

Since the addition of dry nitrogen led to an evaporation of water from the reaction solution, the nitrogen was wetted.

Figure 10:
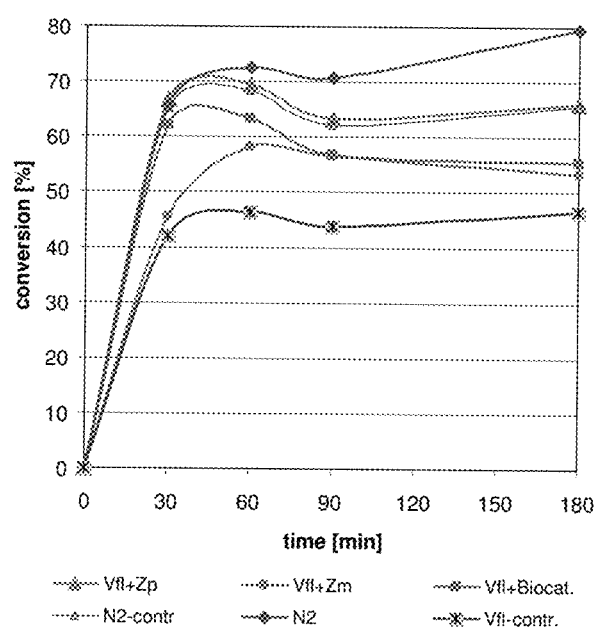
FIG. 10 shows the relative conversion of B3OP to B3AP dependent upon $N_2$-presence.

FIG. 10 shows the calculated relative B3AP conversions. The control with antifoam A ($N_2$-control: Vfl-TA, Zpa-PDC, antifoam, no nitrogen $N_2$) without nitrogen addition corresponds exactly to the reaction run without antifoam A (Vfl-TA, ZpaPDC). Thus, the enzymes are not influenced by the addition of the antifoam concentrate. The run (run $N_2$: Vfl-TA, Zpa-PDC, antifoam, $N_2$) treated with nitrogen showed an increased conversion after 60, 90 and 180 minutes.

EXAMPLE 12

Asymmetric B3AP Synthesis Under Various Conditions

Reaction Conditions:
Final volume: 1 ml
37 µl Vfl-transaminase
32 units/ml Zpa-PDC or Biocatalytics PDC or 3.2 units/ml Zmo PDC
5 mM B3OP
500 mM L-alanine
Cofactors 0.1 mM PLP and TPP, 5 mM $MgCl_2$
pH 7, sodium phosphate FIG. 10 shows the conversion of B3OP to B3AP for the above-identified reaction runs combining the Vfl-transaminase with each PDC.

In FIG. 10 the run designated N2 is the run containing Vfl-transaminase and Zpa-PDC treated with nitrogen and antifoam A. The N2 control is a sample containing Vfl-transaminase, Zpa-PDC and antifoam A without nitrogen treatment. It is evident that there is a significant increase in conversion from the N2 control to the N2-sample due to the presence of nitrogen, which has been fed into the reaction solution. Thus, feeding nitrogen in gaseous form into the reaction medium significantly increases the conversion from B3OP to B3AP.

EXAMPLE 13

Asymmetric Synthesis of B3AP in the Presence of Alcohol Dehydrogenase (ADH)

To remove the acetaldehyde produced by the PDC reaction from the reaction mixture, ADH can be used to convert the acetaldehyde to ethanol.
Reaction Conditions:
110 mM L-alanine
5 mM B3OP
37 µl/ml Vfl-transaminase
32 units/ml Zpa PDC
0.1 mM PLP and TPP
5 mM $MgCl_2$
Sodium phosphate buffer, pH 7
The following reaction runs are shown:
Reaction run 1: reaction with PDC and transaminase
Reaction run 2: reaction with PDC and transaminase with 5 mM ethanol (final concentration) and NADH-addition
Reaction run 3: reaction with PDC, ADH and NADH The ADH used was the ADH from *Saccharomyces cerevisae* with an activity between 50 and 100 units/ml. The PDC-activity was 32 units/ml.

At the beginning of the reaction absolute ethanol has been added to reaction run 2 in a final concentration of 5 mM. At the beginning of the reaction 5 µmol NADH were added to the reaction runs 2 and 3 corresponding to a final concentration of 5 mM NADH. After 10 minutes each, a further addition of 2.4 µmol NADH (4 µl of a 0.6 M NADH-solution in 50 mM phosphate buffer, pH 8.5) was added. The NADH solution was stored in ice and prepared immediately before use.

Figure 11:
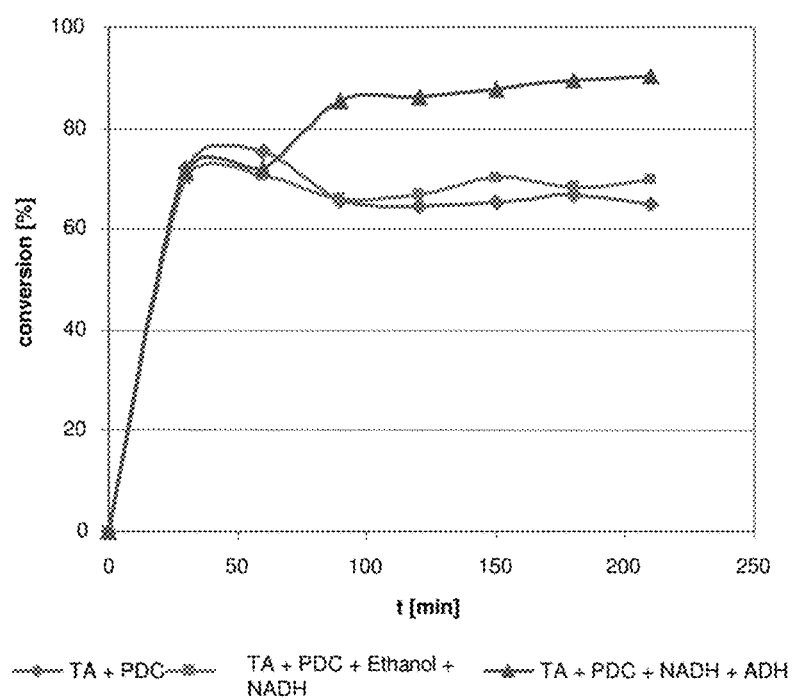
FIG. 11 shows the relative conversion of B3OP to B3AP in the presence of an ADH.

The results are given in FIG. 11 and table 5. The effect of the ADH is clearly evident. The conversion increases up to approximately 90%. Control run 2 without ADH and 5 mM ethanol only slightly deviates from control run 1. Thus, the addition of ADH greatly increases the conversion in the asymmetric synthesis of B3AP from B3OP.

What is claimed is:

1. A process for the preparation of a compound selected from a group consisting of 3-aminopyrrolidone derivatives, chephalosporine, derivatives of cephalosporine, heterocyclic boronic acids, L-dihydroxphenylalanine (L-Dopa), α-methyldopa, D-phenylglycine, β-hydroxyphenylglycine, phosphinothricine, pyrimido derivatives and pyrrolidone derivatives, the process comprising:
   a) providing an amino acceptor and an amino donor,
   b) reacting the amino acceptor and the amino donor with a transaminase,
   c) obtaining a desired optically active chiral amine and a ketone by-product, and
   d) converting the optically active chiral amine to the compound, and
   wherein the amino acceptor is selected from a group consisting of phenylpyruvic acid, a salt thereof, pyruvic acid, a salt thereof, 2-ketoglutarate, 3-oxobutyrate, 2-butanone, 3-oxopyrrolidine, 3-pyridylmethylketone, 3-oxobutyric acid ethyl ester, 3-oxopentanoic acid methyl ester, N-1-boc-3-oxopiperidinone, N-1-boc-3-oxopyrrolidine, 3-oxo-piperidine, alkyl-3-oxo-butonoates, methoxy-acetone and 1-oxotetralone.

2. The process according to claim 1, wherein the transaminase is a (R)- or (S)-selective transaminase.

3. The process according to claim 1, wherein the amino donor is selected from the group consisting of amines or amino acids, in particular from β-alanine, alanine, α-methylbenzylamine (α-MBA), glutamate, phenylalanine and γ-aminobutyrate, glycin, 3-aminobutyrate, isopropylamine, 2-aminobutane and a salt, for instance a chloride, of any one thereof.

4. The process according to claim 1, wherein the obtained amines are amines, in particular mono- or bicyclic amines, in particular amines of 5 to 6-membered cyclic or S-, O-, or N-substituted heterocyclic hydrocarbons or aromatic amines, in particular alkyl- or alkoxy-substituted aromatic amines.

5. The process according to claim 1, wherein the obtained amines are selected from the group consisting of phenylalanine, alanine, 3-am inopiperidine, alkyl-3-amino-butanoates, 3-aminopyrrolidine (3-AP), 3-pyridyl-1-ethylamine (3-PEA), N-1-boc-3-aminopyrrolidine (B3AP), 3-aminobutyric acid ethyl ester (3-ABEE), 3-aminopentanoic acid methyl ester (3-APME), α-methylbenzylamine (α-MBA), 1-aminotetraline, α-methyl-4-(3-pyridyl)-butanamine, glutamate, β-aminobutyrate, sec-butylamine, methoxyisopropylamine, derivatives of 3-aminopyrrolidine, 1-N-boc-3-aminopiperidin, cephalosporine and derivatives of cephalosporine.

6. The process according to claim 1, wherein the transaminase is from *Vibrio fluvialis, Alcaligenes denitrificans, Klebsiella pneumoniae* or *Bacillus thuringiensis*.

7. The process according to claim 1, wherein the ketone by-product obtained in step c is pyruvate.

8. The process according to claim 1, wherein the ketone by-product obtained in step c) is in a further process step e) removed from by reaction with at least one enzyme.

9. The process according to claim 8, wherein the enzyme used in step e) is a decarboxylase.

10. The process according to claim 8, wherein the at least one enzyme used in step e) is a synthase.

11. The process according to claim 8, wherein the enzyme used in step e) is a dehydrogenase.

12. The process according to claim 8, wherein the enzyme is a pyruvate decarboxylase (PDC).

13. The process according to claim 8, wherein the enzyme is a lactate dehydrogenase (LDH).

14. The process according to claim 8, wherein the enzyme is an acetolactate synthase.

15. The process according to claim 12, wherein acetaldehyde formed by the action of the PDC is removed.

16. The process according to claim 15, where acetaldehyde is removed by reaction with at least one enzyme.

17. The process according to claim 16, wherein the enzyme is an alcohol dehydrogenase.

18. The process according to claim 15, wherein the acetaldehyde is removed by feeding gaseous nitrogen into the reaction mixture.

19. The process according to claim 15, wherein the acetaldehyde is removed by applying a reduced pressure to the reaction mixture.

20. The process according to claim 15, wherein the acetaldehyde is removed by chemical methods.

21. The process according to claim 1, further comprising removing the optically active chiral amine obtained in step c).

22. The process according to claim 1, wherein the process is carried out in a reaction mixture having a pH from 5.0 to 9.5, preferably 6.0 to 7.0, preferably 6.0 to 6.9.

23. The process according to claim 1, wherein the process is carried out for a reaction time of 40 to 70 minutes.

24. A process for the preparation of a compound selected from 3-aminopyrrolidone derivatives, the process comprising:
   a) providing an amino acceptor and an amino donor,
   b) reacting the amino acceptor and the amino donor with a transaminase,
   c) obtaining a desired optically active chiral amine and a ketone by-product, and
   d) converting the optically active chiral amine to the compound, and
   wherein the amino acceptor is N-1-boc-3-oxopyrrolidine.

25. The process according to claim 1, wherein the amino donor is alanine.

26. The process according to claim 12, wherein the acetaldehyde formed by the reaction of the PDC is removed by feeding gaseous nitrogen ($N_2$) into the reaction mixture.

27. The process according to claim 12, wherein the reaction is carried out in the presence of at least one pyruvate decarboxylase and at least one alcohol dehydrogenase.

28. The process according to claim 12, wherein the reaction is carried out in the presence of at least one pyruvate decarboxylase, at least one alcohol dehydrogenase and additionally in the presence of gaseous nitrogen ($N_2$).

* * * * *